United States Patent
Prakash et al.

[11] Patent Number: 6,129,942
[45] Date of Patent: Oct. 10, 2000

[54] SWEETENER SALTS OF N-[N-(3,3-DIMETHYLBUTYL)-L-α-ASPARTYL]-L-PHENYLALANINE 1-METHYL ESTER

[75] Inventors: Indra Prakash, Hoffman Estates; Zhi Guo, Chicago, both of Ill.

[73] Assignee: The NutraSweet Company, Chicago, Ill.

[21] Appl. No.: 09/148,134

[22] Filed: Sep. 4, 1998

Related U.S. Application Data

[60] Provisional application No. 60/058,507, Sep. 11, 1997.
[51] Int. Cl.[7] .................................................. A23L 1/236
[52] U.S. Cl. ............................... 426/548; 560/40; 560/41
[58] Field of Search .............................. 426/548; 560/40, 560/41

[56] References Cited

U.S. PATENT DOCUMENTS

| | | | |
|---|---|---|---|
| 4,029,701 | 6/1977 | Haas | 426/548 |
| 4,031,258 | 6/1977 | Haas | 426/548 |
| 4,153,737 | 5/1979 | Berg | 426/548 |
| 4,448,716 | 5/1984 | Tsau | 260/112.5 |
| 5,480,668 | 1/1996 | Nofre | 426/548 |
| 5,510,508 | 4/1996 | Claude | 560/41 |
| 5,728,862 | 3/1998 | Prakash | 560/40 |

FOREIGN PATENT DOCUMENTS

| | | |
|---|---|---|
| 768041 | 4/1997 | European Pat. Off. . |
| 86-04766 | 8/1986 | Spain . |

OTHER PUBLICATIONS

T.P. Labuza et al., "The Kinetics of Nonenzymatic Browning", Physical Chemistry of Foods, Chapter 14, pp. 595–649, Marcell Dekker, Inc., New York (1992).

E. Benedetti et al., "The Structure of New Peptide Taste Ligands", Structure, Folding, and Conformational Analysis, P233, Amer. Peptide Symp., Nashville, Tennessee (1997).

*Primary Examiner*—Leslie Wong
*Attorney, Agent, or Firm*—Fitzpatrick, Cella, Harper & Scinto

[57] ABSTRACT

Dipeptide sweeteners are disclosed that are sweetener salts of N-[N-(3,3-dimethylbutyl)-L-α-aspartyl]-L-phenylalanine 1-methyl ester represented by the formula

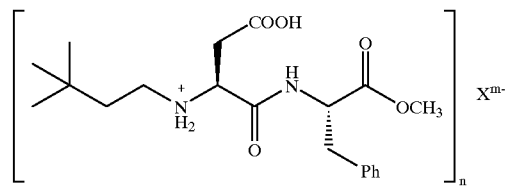

wherein $X^{m-}$ is a conjugate base derived by deprotonation of an acidic sweetener, preferably saccharin, acesulfame, cyclamic acid and glycyrrhizic acid; and m=n. Also disclosed is a liquid low-calorie sweetener containing such basic salts.

6 Claims, 1 Drawing Sheet

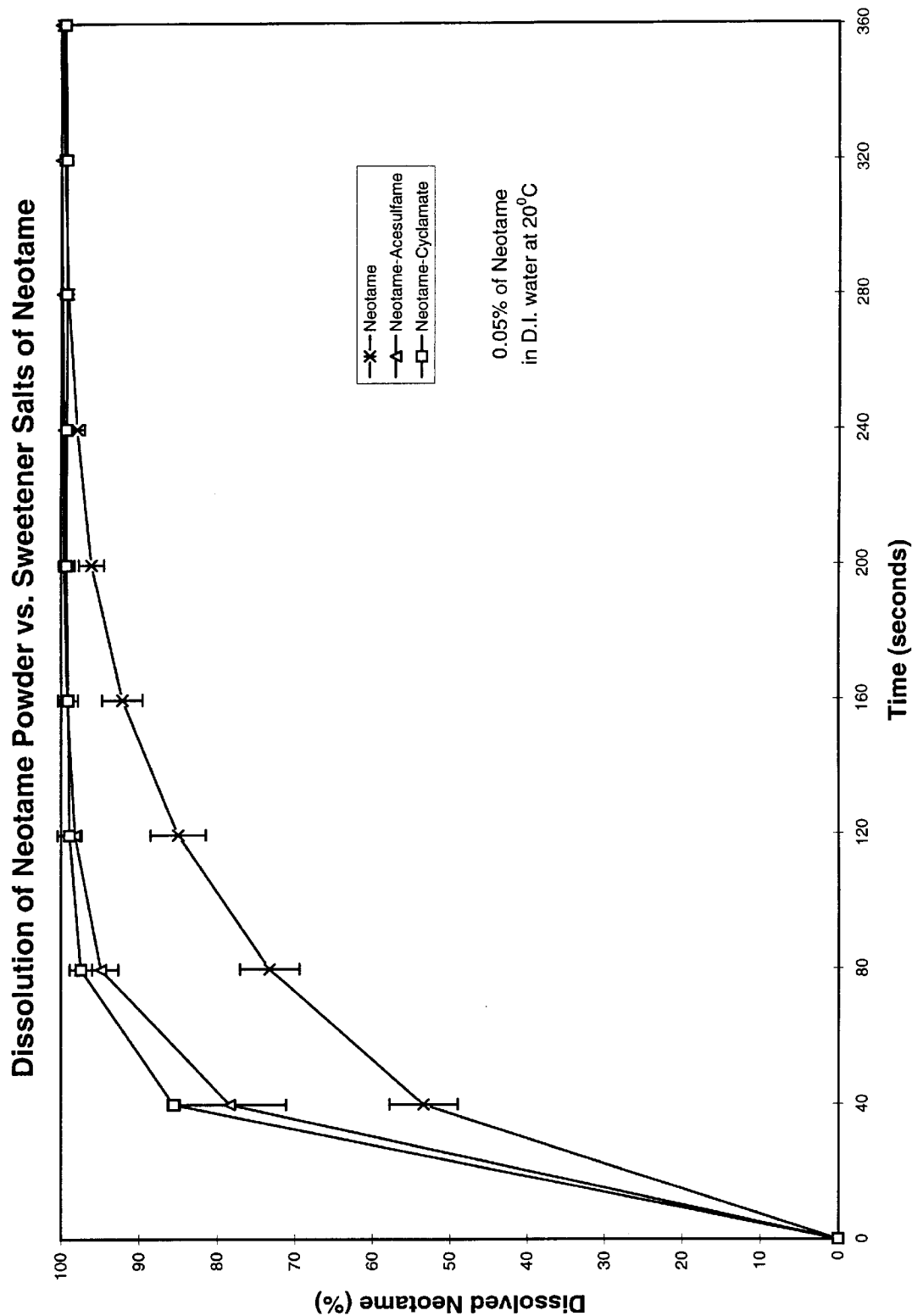

SWEETENER SALTS OF N-[N-(3,3-DIMETHYLBUTYL)-L-α-ASPARTYL]-L-PHENYLALANINE 1-METHYL ESTER

This invention claims the benefit of U.S. Provisional Application Ser. No. 60/058,507, filed Sep. 11, 1997.

BACKGROUND OF THE INVENTION

1. Field of the Invention

This invention relates to novel sweeteners. In particular, the invention relates to sweetener salts of the N-alkylated aspartame derivative, N-[N-(3,3-dimethylbutyl)-L-α-aspartyl]-L-phenylalanine 1-methyl ester, i.e., neotame. The invention also relates to a liquid low calorie sweetener containing such sweetener salts.

2. Related Background Art

It is known that various N-substituted derivatives of aspartame, such as disclosed in U.S. Pat. No. 5,480,668, are useful as sweetening agents. In particular, the N-alkylated aspartame derivative, N-[N-(3,3-dimethylbutyl)-L-α-aspartyl]-L-phenylalanine 1-methyl ester, is known as an extremely potent sweetening agent since its sweetening potency, on a weight basis, has been reported to be at least 50 times that of aspartame and about 10,000 times that of sucrose.

Since sweetening agents are often employed in aqueous solutions and beverages, it is important that they have an acceptable dissolution rate and an effective level of solubility to be commercially practicable. U.S. Pat. No. 4,031,258 describes certain inorganic salts of dipeptide sweeteners that provide improved dissolution and solubility. European Patent Application No. EP 768,041 and Spanish Patent 85-547855 disclose salts formed between aspartame and acidic sweetener compounds, such as saccharin, cyclamic acid and acesulfame. It is said that these sweetener salts have improved sucrose-like taste. Salts of N-[N-(3,3-dimethylbutyl)-L-α-aspartyl]-L-phenylalanine 1-methyl ester, however, are not disclosed or suggested in either reference.

It is known that the physical properties, as well as the stability of aspartame and other peptides can be modified by conversion to their salts. This is disclosed, for example, in U.S. Pat. Nos. 4,031,258 and 4,153,737. U.S. Pat. No. 4,173,737 also describes concentrated liquid low calorie sweeteners.

Structurally, however, N-[N-(3,3-dimethylbutyl)-L-α-aspartyl]-L-phenylalanine 1-methyl ester and aspartame differ in that, in N-[N-(3,3-dimethylbutyl)-L-α-aspartyl]-L-phenylalanine 1-methyl ester, a bulky neohexyl substituent is present on the amine nitrogen.

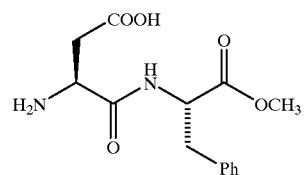
Aspartame

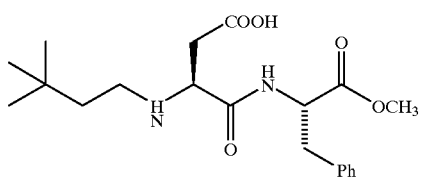
Neotame

This structural difference results in dramatic differences in the physical and chemical properties of these compounds. For example, the melting point of N-[N-(3,3-dimethylbutyl)-L-α-aspartyl]-L-phenylalanine 1-methyl ester is 80° C., while that of aspartame is 248° C. In addition, N-[N-(3,3-dimethylbutyl)-L-α-aspartyl]-L-phenylalanine 1-methyl ester has much higher solubility in organic solvents than aspartame, and a much lower solubility in water. It is also known that N-[N-(3,3-dimethylbutyl)-L-α-aspartyl]-L-phenylalanine 1-methyl ester has a higher stability than aspartame under some pH conditions, as described in U.S. Pat. No. 5,480,688. The pronounced difference in sweetness between the two compounds is further evidence of their chemical dissimilarity.

Moreover, it is also known that a primary amino group such as the one on aspartame (pKa 7.7) generally has a different pKa than those from a secondary amino group such as the one on N-[N-(3,3-dimethylbutyl)-L-α-aspartyl]-L-phenylalanine 1-methyl ester (pKa 8.1). Moreover, the pKa's of an amino acid are known to have a profound impact on food applications (Labuza, T. P. and Basisier, M. W., 1992, "Physical Chemistry of Foods", H. G. Schwartzber and R. W. Hartel (Eds.), Marcel Dekker, Inc., New York). It is also well known that a secondary amine group can not form Schiff base type compounds with carbonyl compounds while a primary amine may. Furthermore, N-[N-(3,3-dimethylbutyl)-L-α-aspartyl]-L-phenylalanine 1-methyl ester exhibits physiologically different behavior than aspartame as exemplified by the dramatic difference in sweetness. These differences are clearly indicative that the characteristics and properties of one can not be said to suggest those of the other.

While N-[N-(3,3-dimethylbutyl)-L-α-aspartyl]-L-phenylalanine 1-methyl ester is a highly potent sweetener, it is sparingly soluble in water and can give rise to dusting problems. It is also would be desirable to modify and improve the taste properties of N-[N-(3,3-dimethylbutyl)-L-α-aspartyl]-L-phenylalanine 1-methyl ester to accommodate a specific application. Therefore, there is a need for N-[N-(3,3-dimethylbutyl)-L-α-aspartyl]-L-phenylalanine 1-methyl ester derivatives that have improved taste, good dissolution and solubility properties in aqueous systems, and avoid dusting problems often encountered with fine powders. By forming salts with acidic sweeteners, one may be able to achieve such properties.

SUMMARY OF THE INVENTION

This invention relates to dipeptide sweeteners that are sweetener salts of N-[N-(3,3-dimethylbutyl)-L-α-aspartyl]-L-phenylalanine 1-methyl ester possessing good dissolution and solubility properties in aqueous systems. In particular, the salts of N-[N-(3,3-dimethylbutyl)-L-α-aspartyl]-L-phenylalanine 1-methyl ester of this invention are represented by the formula

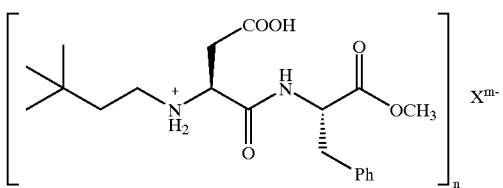

wherein $X^{m-}$ is selected from the group consisting of the conjugate bases derived by deprotonation of acidic sweeteners, preferably saccharin, acesulfame, cyclamic acid or glycyrrhizic acid; and m=n. Preferably n is 1, 2 or 3. The invention is also related to a liquid low calorie sweetener containing the salts of this invention.

BRIEF DESCRIPTION OF THE DRAWING

The FIGURE is a graph comparing the aqueous dissolution of N-[N-(3-dimethylbutyl)-L-α-aspartyl]-L-phenylalanine 1-methyl ester at a target concentration of 0.05% by weight with equivalent neotame concentrations, i.e., the concentration of the neotame delivered in each case is the same, of the acesulfame and cyclamate salts of N-[N-(3-dimethylbutyl)-L-α-aspartyl]-L-phenylalanine 1-methyl ester.

DETAILED DESCRIPTION OF THE INVENTION

This invention is directed to sweetener salts of N-[N-(3, 3-dimethylbutyl)-L-α-aspartyl]-L-phenylalanine 1-methyl ester, i.e., sweetener salts of neotame. U.S. Pat. No. 5,480, 668, U.S. Pat. No. 5,510,508 and U.S. Pat. No. 5,728,862, which describe the preparation of N-[N-(3,3-dimethylbutyl)-L-α-aspartyl]-L-phenylalanine 1-methyl ester are incorporated by reference herein as if fully set forth. Thus, the starting material may be readily prepared by one of ordinary skill in the art without undue experimentation.

The sweetener salts of this invention may be prepared by adding N-[N-(3,3-dimethylbutyl)-L-α-aspartyl]-L-phenylalanine 1-methyl ester and an acidic sweetener compound to an amount of a solvent effective to dissolve both the N-[N-(3,3-dimethylbutyl)-L-α-aspartyl]-L-phenylalanine 1-methyl ester and the acidic compound, and then stirring for a period of time to achieve formation of a salt. Suitable solvents include ethanol, methanol, acetone, acetonitrile, ethyl acetate, water and t-butyl methyl ether. The salt product may be recovered by evaporating the solvent in vacuo. The salt product may also be recovered by freeze drying or spray drying the resulting solution. These salts can also be prepared by adding acid (such as hydrochloric acid, sulfuric acid or phosphoric acid) to a slurry of N-[N-(3,3-dimethylbutyl)-L-α-aspartyl]-L-phenylalanine 1-methyl ester and acidic sweetener salt (such as sodium saccharin, potassium salt of acesulfame-K or sodium cyclamate) in a solvent such as water or alcohol. Sweetener salts of N-[N-(3,3-dimethylbutyl)-L-α-aspartyl]-L-phenylalanine 1-methyl ester prepared under these condition do not show any racemization.

The acidic sweetener compounds employed in the preparation of the salts of this invention are typically selected from sweetener compounds that have a pKa effectively lower than the pKa of the amine functionality of N-[N-(3, 3-dimethylbutyl)-L-α-aspartyl]-L-phenylalanine 1-methyl ester to result in the formation of the desired salt. Such compounds include, for example, saccharin, acesulfame, cyclohexyl sulfamic acid (hereinafter cyclamic acid), and glycyrrhizic acid. As such, $X^{m-}$ is the anionic conjugate base derived by deprotonation of the acidic compound.

Particularly preferred sweetener salts of this invention include the salts formed between N-[N-(3,3-dimethylbutyl)-1-L-α-aspartyl]-L-phenylalanine 1-methyl ester and an acidic sweetener chosen from the group consisting of saccharin, acesulfame, cyclamic acid and glycyrrhizic acid.

It is believed that the salts of this invention provide a number of improved properties over those of N-[N-(3,3-dimethylbutyl)-L-α-aspartyl]-L-phenylalanine 1-methyl ester. In particular, the aqueous solubility is increased and the dissolution rate of the composition is greatly improved. These sweetener salts of neotame are sweet in taste. It is also believed that these salts will have improved taste. Thus, the salts of N-[N-(3,3-dimethylbutyl)-L-α-aspartyl]-L-phenylalanine 1-methyl ester will be particularly useful in beverage systems, particularly since additional methods or mechanical preparations are diminished or not necessary to provide for quick dissolution such as desired in a table top sweetener. The salts of this invention may be admixed with known bulking agents to prepare tablets, powdered and granular sweeteners using methods well known to those skilled in the art. Another advantage of the salts of this invention is that they do not exhibit the dusting problems associated with N-[N-(3,3-dimethylbutyl)-L-α-aspartyl]-L-phenylalanine 1-methyl ester.

The salts may also be used to prepare a liquid, low-calorie sweetener by dissolving a high concentration of the sweetener salt of this invention in an aqueous or alcoholic system, e.g., water, propylene glycol, a water/propylene glycol mixture, ethanol or a water/ethanol mixture. Such a liquid, low-calorie sweetener may find utility in such foodstuffs as gelatin desserts, fruit flavored beverages, cereal, cake mixes, fruit juices, syrups, salad dressings, pet foods, carbonated soft drinks, table top sweeteners and the like. Such utilities are not restrictive since other applications may include cough medicines, tonics and the like. One embodiment of this invention of particular interest contemplates a liquid table top sweetener as a replacement for sucrose and other known sweeteners. The liquid low calorie sweetener generally will contain up to about 40% by weight of the salt of N-[N-(3,3-dimethylbutyl)-L-α-aspartyl]-L-phenylalanine 1-methyl ester, the concentration depending, of course, on the desired end use.

The Examples which follow are intended as an illustration of certain preferred embodiments of the invention, and no limitation of the invention is implied.

EXAMPLE 1

Acesulfame Salt of N-[N-(3,3-dimethylbutyl)-L-α-aspartyl]-L-phenylalanine 1-methyl ester Acesulfame (6.30 g, 0.0386 mol) and N-[N-(3,3-dimethylbutyl)-L-α-aspartyl]-L-phenylalanine 1-methyl ester (15.31 g, 0.0386 mol) were dissolved in methanol (100 ml) at room temperature to form a clear solution. The bulk of the methanol was removed using a rotary evaporator at 33° C. under house vacuum. The residual solvent was removed using a mechanical pump. The yield of the title compound was 20.97 g. The acesulfame salt of N-[N-(3,3-dimethylbutyl)-L-α-aspartyl]-L-phenylalanine 1-methyl ester (0.2 g) dissolved in water (100 ml) in less than 120 seconds (visual observation).

Water content (Karl Fisher): 1.81%.

Anal. Calcd for $C_{24}H_{35}N_3O_9S \cdot 0.55H_2O$: C,52.27; H,6.60; N,7.62; S,5.81. Found: C,52.55; H,6.50; N,7.64; S,5.91.

$^1$H NMR (DMSO-$d_6$): δ 0.81(S,9H,t-butyl), 1.42(m, 2H,—CH$_2$—), 1,89(s,3H,CH$_3$—C=C), 2.6–3.1 (m,6H,—CH$_2$—), 3.62(s,3H,CH$_3$—O), 4.06(m,1H,—CH—), 4.59(m, 1H,—CH—), 5.27(s,1H,H—C=C), 7.2–7.3(m,5H, phenyl).

EXAMPLE 2

Saccharin Salt of N-[N-(3,3-dimethylbutyl)-L-α-aspartyl]-L-phenylalanine 1-methyl ester Saccharin (7.62 g, 0.0416 mol) and N-[N-(3,3-dimethylbutyl)-L-α-aspartyl]-L-phenylalanine 1-methyl ester (16.42 g, 0.0416 mol) were dissolved in methanol (100 ml) at room temperature to form a clear solution. The bulk of the methanol was removed using a rotary evaporator at 33° C. under house vacuum. The residual solvent was removed using a mechanical pump. The yield of the title compound was 23.30 g. The saccharin salt of neo-α-aspartame (0.2 g) dissolved in water (100 ml) in less than 120 seconds (visual observation).

Water content (Karl Fisher): 1.16%.

Anal. Calcd for $C_{27}H_{35}N_3O_8S \cdot 0.37H_2O$: C,57.06; H,6.34; N,7.39; S,5.64. Found: C,57.23; H,6.30; N,7.42; S,5.69.

$^1$H NMR (DMSO-$d_6$): δ 0.80(s,9H,t-butyl), 1.42(m,2H,—CH$_2$—), 2.5–3.1(m,6H, CH$_2$—), 3.62(s,3H,CH$_3$—O), 4.05 (m,1H,—CH—), 4.58(m,1H,—CH), 7.1–7.7(m,9H,phenyl).

EXAMPLE 3

Cyclamic Acid Salt of N-[N-(3,3-dimethylbutyl)-L-α-aspartyl]-L-phenylalanine 1-methyl ester Cyclamic acid (7.33 g, 0.0409 mol) and N-[N-(3,3-dimethylbutyl)-L-α-aspartyl]-L-phenylalanine 1-methyl ester (16.22 g, 0.0409 mol) were dissolved in methanol (100 ml) at room temperature to form a clear solution. The bulk of the methanol was removed using a rotary evaporator at 33° C. under house vacuum. The residual solvent was removed using a mechanical pump. The yield of the title compound was 22.75 g. The cyclamic salt of N-[N-(3,3-dimethylbutyl)-L-α-aspartyl]-L-phenylalanine 1-methyl ester (0.2 g) dissolved in water (100 ml) in less than 120 seconds (visual observation).

Water content (Karl Fisher): 0.94%.

Anal. Calcd for $C_{26}H_{43}N_3O_8S \cdot 0.29H_2O$: C,55.47; H,7.80; N,7.46; S,5.70. Found: C,55.68; H,7.72; N,7.48; S,5.69.

$^1$H NMR (DMSO-$d_6$): δ 0.80(s,9H,t-butyl), 1.0–2.0(m, 12H,—CH$_2$—), 2.5–3.1(m,7H,—CH$_2$— and —CH—), 3.62 (s,3H,CH$_3$—O), 3.90(m,1H,—CH—), 4.57(m,1H,—CH—), 7.1–7.3(m,5H,phenyl).

Comparative Example 1

Dissolution of N-[N-(3,3-dimethylbutyl)-L-α-aspartyl]-L-phenylalanine 1-methyl ester in Water N-[N-(3,3-dimethylbutyl)-L-α-aspartyl]-L-phenylalanine 1-methyl ester (0.1–0.2 g) was dissolved in water (100 mL). The compound completely dissolved in 5–8 minutes (visual observation). The dissolution of 1.0 g of N-[N-(3,3-dimethylbutyl)-L-α-aspartyl]-L-phenylalanine 1-methyl ester in 100 mL of water required approximately 45 minutes.

Other variations and modifications of this invention will be obvious to those skilled in this art. This invention is not to be limited except as set forth in the following claims.

What is claimed is:

1. A salt of N-[N-(3,3-dimethylbutyl)-L-aspartyl]-L-phenylalanine 1-methyl ester represented by the formula $$\left[ \begin{array}{c} \text{structure with COOH, } \overset{+}{N}H_2, \text{ OCH}_3, \text{ Ph groups} \end{array} \right]_n X^{m-}$$

wherein $X^{m-}$ is a conjugate base derived by deprotonation of an acidic sweetener and m=n.

2. A salt according to claim 1, wherein n is 1, 2 or 3.

3. A salt according to claim 1, wherein n is 1 and $X^{m-}$ is a conjugate base derived by deprotonation of an acidic sweetener selected from the group consisting of saccharin, acesulfame, cyclamic acid and glycyrrhizic acid.

4. A liquid low-calorie sweetener composition comprising a salt of a dipeptide-sweetener represented by the formula $$\left[ \begin{array}{c} \text{structure with COOH, } \overset{+}{N}H_2, \text{ OCH}_3, \text{ Ph groups} \end{array} \right]_n X^{m-}$$

wherein $X^{m-}$ is a conjugate base derived by deprotonation of an acidic sweetener, and m=n, dissolved in a consumable solvent or solvents in a concentration up to about 40% by weight of the composition to provide a high concentration liquid low-calorie sweetener.

5. A liquid low-calorie sweetener according to claim 4, wherein the solvent is ethanol.

6. A liquid low-calorie sweetener according to claim 4, wherein n is 1 and $X^{m-}$ is a conjugate base derived by deprotonation of an acidic sweetener selected from the group consisting of saccharin, acesulfame, cyclamic acid and glycyrrhizic acid.

* * * * *

UNITED STATES PATENT AND TRADEMARK OFFICE
CERTIFICATE OF CORRECTION

PATENT NO. : 6,129,942
DATED : October 10, 2000
INVENTOR(S) : Indra Prakash et al.

It is certified that error appears in the above-identified patent and that said Letters Patent is hereby corrected as shown below:

ON THE COVER PAGE [56] References Cited
After "T.P. Labuza et al.": "Marcell Dekker, Inc.," should read --Marcel Dekker, Inc.--;

COLUMN 1:
Line 50, "4,173,737" should read --4,153,737--;

COLUMN 2
Line 47, delete "is".

Signed and Sealed this

Twelfth Day of June, 2001

*Attest:*

NICHOLAS P. GODICI
*Attesting Officer*     Acting Director of the United States Patent and Trademark Office